United States Patent
Wilkins

(10) Patent No.: US 11,285,289 B2
(45) Date of Patent: Mar. 29, 2022

(54) SELF-SANITIZING MEDICAL DEVICES, SYSTEMS AND METHODS USING THE SAME

(71) Applicant: SOCLEAN, INC., Peterborough, NH (US)

(72) Inventor: Robert Wilkins, Peterborough, NH (US)

(73) Assignee: SOCLEAN, INC., Peterborough, NH (US)

(*) Notice: Subject to any disclaimer, the term of this patent is extended or adjusted under 35 U.S.C. 154(b) by 0 days.

(21) Appl. No.: 17/245,789

(22) Filed: Apr. 30, 2021

(65) Prior Publication Data

US 2021/0338967 A1 Nov. 4, 2021

Related U.S. Application Data

(60) Provisional application No. 63/019,084, filed on May 1, 2020.

(51) Int. Cl.
*A61M 16/10* (2006.01)
*A61M 16/16* (2006.01)
(Continued)

(52) U.S. Cl.
CPC ........ *A61M 16/1065* (2014.02); *A61L 2/202* (2013.01); *A61M 16/0816* (2013.01);
(Continued)

(58) Field of Classification Search
CPC .............. A61M 16/00; A61M 16/0003; A61M 16/0057; A61M 16/0066; A61M 16/06; A61M 16/0816; A61M 16/10; A61M 16/105; A61M 16/1065; A61M 16/16; A61M 2202/0216; A61M 2209/10; A61L 2/202; A61L 2202/24

See application file for complete search history.

(56) References Cited

U.S. PATENT DOCUMENTS

| 11,000,611 B1 * | 5/2021 | He ................. A61M 16/0666 |
| 2005/0133031 A1 * | 6/2005 | Han ................. A61M 16/0808 128/204.17 |

(Continued)

OTHER PUBLICATIONS

International Search Report from related international application No. PCT/US21/30173, dated Aug. 5, 2021, 2 pages.
(Continued)

*Primary Examiner* — Joseph D. Boecker
(74) *Attorney, Agent, or Firm* — Grossman, Tucker, Perrault & Pfleger, PLLC

(57) ABSTRACT

Technologies (e.g., devices, systems and methods) for sanitizing positive airway pressure (PAP) systems are described. In some embodiments, the technologies include a PAP delivery system comprising a hose and a PAP mask, a positive pressure supply system configured to generate a flow of pressurized air which is delivered to a user through the hose to the PAP mask of the PAP delivery system, a sanitizing system configured to sanitize one or more components of the self-sanitizing PAP system, and a PAP base unit housing, wherein one or more components of the positive pressure supply system and the sanitizing system are disposed at least partially within the PAP base unit housing.

24 Claims, 8 Drawing Sheets

(51) Int. Cl.
　　　A61L 2/20　　　(2006.01)
　　　A61M 16/08　　(2006.01)
(52) U.S. Cl.
　　　CPC .......... *A61M 16/16* (2013.01); *A61L 2202/24* (2013.01); *A61M 2205/3331* (2013.01)

(56) References Cited

U.S. PATENT DOCUMENTS

| | | | |
|---|---|---|---|
| 2013/0216627 A1* | 8/2013 | Galbraith | B01D 53/047 424/600 |
| 2014/0154134 A1* | 6/2014 | Leyva | A61L 2/183 422/28 |
| 2014/0158128 A1* | 6/2014 | Heimel | A61M 16/109 128/203.26 |
| 2015/0044094 A1* | 2/2015 | Cadieux | A61L 2/20 422/28 |
| 2016/0235876 A1* | 8/2016 | Leyva | A61L 2/202 |
| 2018/0028770 A1 | 2/2018 | Parrish | |
| 2018/0153230 A1* | 6/2018 | Verner | A61L 9/12 |
| 2019/0336627 A1 | 11/2019 | Lucio | |
| 2021/0196850 A1* | 7/2021 | Maw | A61M 16/0875 |
| 2021/0322608 A1* | 10/2021 | Lanier | A61L 2/202 |

OTHER PUBLICATIONS

Al Ashry, et al. "Humidification during Mechanical Ventilation in the Adult Patient", vol. 2014, Article ID 715434, Hindawi Publishing Corporation, BioMed Research International.

* cited by examiner

SELF-SANITIZING MEDICAL DEVICES, SYSTEMS AND METHODS USING THE SAME

CROSS REFERENCE TO RELATED APPLICATIONS

This Application claims priority to U.S. Provisional Application No. 63/019,084, filed May 1, 2020, the entire content of which is incorporated herein by reference.

FIELD

The present disclosure generally relates to self-sanitizing medical devices. More specifically, the present disclosure relates to self-sanitizing medical devices that include an integral sanitizing gas generator. Devices, systems, and methods using such technologies are also disclosed.

BACKGROUND

Many medical devices include environments that can facilitate undesirable growth of bacteria, and thus must be cleaned periodically in order to remain sanitary for use. For example, sleep apnea is often treated with a positive airway pressure (PAP) equipment, such as a continuous positive airway pressure (CPAP) device. Among other things, a CPAP device can address symptoms of sleep apnea (e.g., reduced oxygen levels in the blood, sleep loss, etc.) by delivering a stream of pressurized air through a hose to a nasal pillow or facemask surrounding a user's nose. By blowing air at a prescribed pressure for a user, the CPAP device can help keep the user's breathing passageways open and unobstructed as the user sleeps.

Many PAP devices include a water reservoir that adds humidity to air that is blown into the user's nose or mouth during use of the device. A warm and humid environment may therefore be present in various components of a PAP device, such as the water reservoir, hose, facemask and/or nasal pillow. Such an environment can facilitate the maintenance and/or growth of bacteria and other pathogens, potentially presenting a health hazard to the user. Even if a PAP device does not include a reservoir, the growth/presence of bacteria and other pathogens may be promoted by the fact that a user often exhales into the into the facemask and/or nose pillow of a PAP device. Bacteria and other pathogens may therefore be conveyed from the user's mouth and/or skin to within passageways within the mask, nose pillow, hose, etc. of the PAP device—where they may proliferate.

Therefore, like many medical devices, PAP devices generally require periodic cleaning and/or maintenance to ensure that they are sanitary for continued use. Many PAP device manufacturers recommend that users perform daily and weekly maintenance on their devices to prevent growth and build-up of bacteria, mold and/or other pathogens in various components of the device, such as the face mask (or nasal pillow), the hoses, the water reservoir, etc. Such maintenance may require each part of the PAP device to be cleaned individually, which many users find difficult and time consuming Consequently, many patients resist using a PAP device, and/or avoid cleaning their PAP device on a regular basis.

Various add-on systems have been developed to make it easier and more convenient for users to sanitize medical equipment, and in particular PAP equipment. For example, the SOCLEAN® devices sold by SOCLEAN® Inc. are an accessory that enables PAP users to easily sanitize their PAP equipment with a sanitizing gas. For example, some versions of SOCLEAN® devices fluidly connect a sanitizing gas generator (e.g., an ozone generator) to one or more components of PAP equipment, such as a PAP hose, a PAP device/reservoir, or a combination thereof. In operation, such devices circulate a sanitizing gas such as ozone through such components, resulting in their effective sanitization.

Although the SoClean® devices are highly effective and commercially successful, the inventors have identified that there is a continued interest in the development of novel devices, systems, and methods for cleaning, sanitizing and disinfecting all or a portion of a medical device, such as a PAP device.

BRIEF DESCRIPTION OF THE DRAWINGS

Reference is now made to the following detailed description which should be read in conjunction with the following figures, wherein like numerals represent like parts.

DETAILED DESCRIPTION

Figure 1:
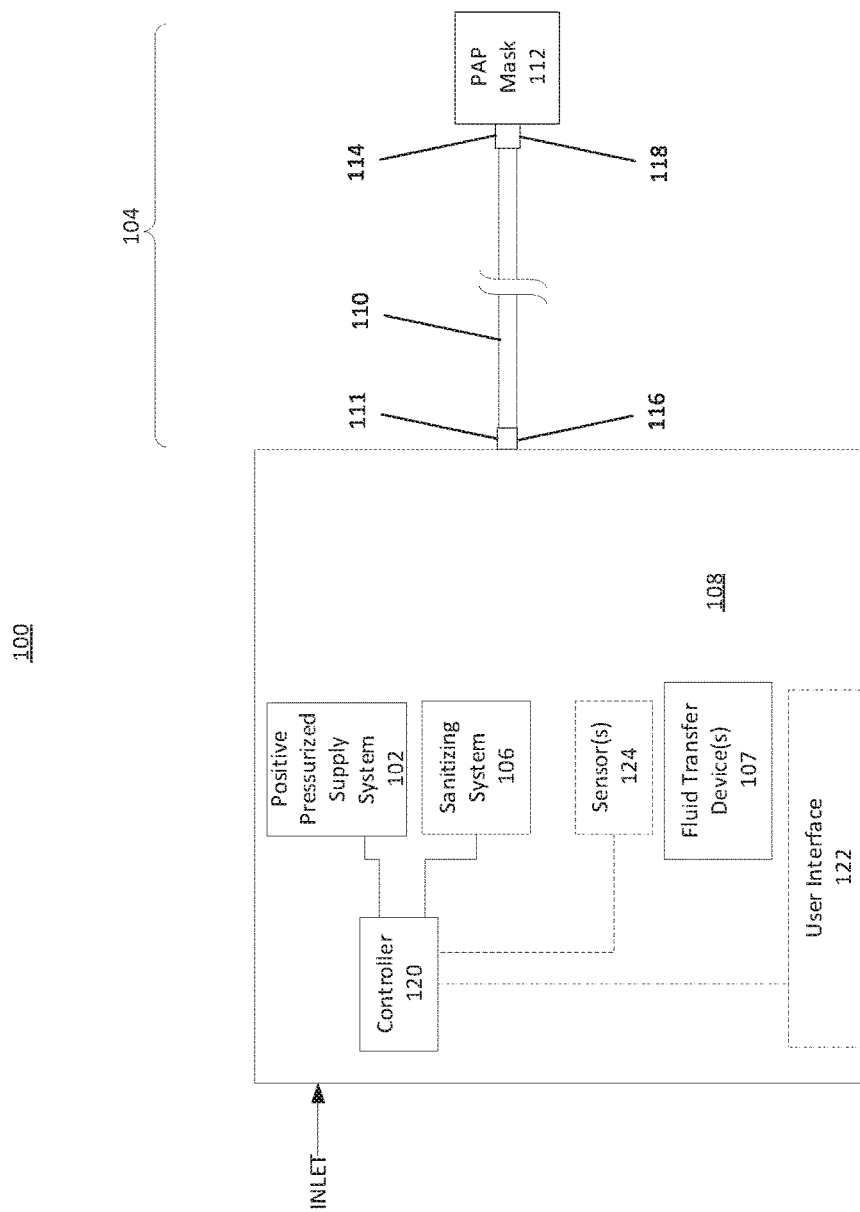
FIG. 1 is schematic view of one example of a self-sanitizing positive airway pressure (PAP) system consistent with the present disclosure.

PAP and other medical devices often require varying degrees of cleaning, disinfection, and/or sterilization so that they are sanitary to use. While there are various known methods for cleaning and sanitizing medical devices such as PAP devices, such methods are often considered inconvenient, messy, and/or time-consuming. Consequently, users often resist cleaning PAP and other medical devices or rush through cleaning protocols, potentially leading to inadequate sanitization.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

With the foregoing in mind, aspects of the present disclosure relate to technologies for self-sanitizing PAP systems. In embodiments, such technologies are in the form of devices, systems and methods that utilize a sanitizing or disinfecting gas to sanitize or disinfect all or a portion of a PAP system, such as but not limited to the reservoir, hose, and/or PAP mask. As will be described in detail later, the devices, systems and methods of the present disclosure are particularly useful for preventing growth of mold and bacteria on or within the reservoir, hose, and/or PAP mask. In addition to enabling the provision of self-sanitizing PAP systems, the technologies described have the additional benefit of giving users confidence that the inside of their PAP system has been sanitized and, thus, the PAP system is safe to use while minimizing or eliminating the spread of contaminants with the pressurized air.

Systems for sanitizing PAP and other medical devices with a sanitizing gas such as ozone ($O_3$) have been developed. For example, systems have been developed that circulate a sanitizing gas into and/or through one or more components of a medical device, such as a PAP hose, PAP device/reservoir, PAP mask, or a combination thereof. While such systems are effective, they may require a user to properly connect the system to the medical device, which some users may find inconvenient. Moreover, the components of some medical devices may interact with the sanitizing gas, which could limit the effectiveness of the sanitizing gas and/or potentially alter the performance and/or properties of such components.

Still further, existing sanitizing systems may rely on the external administration/introduction of sanitizing gas into one or more components of a medical device, such as a PAP reservoir, PAP hose, or a combination thereof. The introduction of sanitizing gas in that manner can present various challenges. For example, with external introduction/administration of sanitizing gas into a medical device, it can be difficult to ensure that an adequate amount of sanitizing gas contacts all the surfaces that a user wishes to sanitize. Moreover, using external introduction/administration, it may be challenging to limit the exposure of sensitive components, the environment, and/or a user to the sanitizing gas. For example, limiting such exposure may entail careful control over the flow of sanitizing gas within the system, which can be challenging.

While the known systems for sanitizing PAP equipment are generally effective, some of these known systems include a sanitizing system that is separate from the PAP equipment that is being sanitized. The PAP equipment is designed and manufactured independently from the sanitizing system, and as a result, some components of the PAP equipment that will be exposed to the sanitizing gas may be made from materials that are incompatible with the sanitizing gas. To solve this problem, the self-sanitizing PAP system consistent with the present disclosure may feature components exposed to the sanitizing gas (such as, but not limited to, seals and the like) that are constructed from materials that are resistant to the sanitizing gas (e.g., materials that are resistant to ozone such as, but not limited to, polypropylene, silicon, and the like). This may not only increase the operational life of the self-sanitizing PAP system, but may also minimize the risk of the sanitizing gas leaking into the environment.

In addition, because the known systems for sanitizing PAP equipment include a sanitizing system that is separate from the PAP equipment that is being sanitized, it may be difficult to ensure safe operation of the PAP equipment and the sanitizing system. As may be appreciated, simultaneous operation of the PAP equipment and the sanitizing system can result in a dangerous situation. Since the PAP equipment is separate and distinct from the sanitizing system and may be manufactured by two different entities, the PAP equipment and the sanitizing system may not be able to communicate with each other.

To solve this problem, the self-sanitizing PAP system consistent with the present disclosure may feature one or more controllers that are configured to ensure that the PAP equipment and the sanitizing system cannot simultaneously operate. In addition, the controller(s) of the present disclosure may be configured to receive signals from one or more sensors to ensure safe operation as described herein.

Another possible disadvantage associated with some known systems for sanitizing PAP equipment is that it may be difficult to sanitize the water within the humidifier portion of the PAP equipment. As may be appreciated, the presence of water may significantly increase the ability of bacteria, mold, and the like to grow. While some known systems for sanitizing PAP equipment are designed to sanitize the water reservoir, these systems often introduce the sanitizing gas through a connector unit disposed between the hose and the PAP base unit. As such, the sanitizing gas must flow upstream from the connector unit and into the humidifier portion. Once there, the sanitizing gas should enter the water in order to sanitize the water reservoir. The sanitizing gas also needs to flow downstream from the connector unit through the hose and/or PAP mask. It may be difficult for the sanitizing gas flow in both directions. In addition, it may be difficult for the sanitizing gas to enter the water, particularly if the sanitizing gas is introduced into the reservoir above the water.

To improve the sanitizing of the humidifier, the pressure of the sanitizing gas within the PAP equipment may be increased. While this may improve sanitization, it may also cause leaks and/or require more sanitizing gas to be used. The higher sanitizing gas pressure also requires additional sanitizing gas to be generated and, consequently, to be absorbed/converted before being released into the atmosphere. The increased quantity of sanitizing gas can also: increase operating costs; require a larger or more expensive sanitizing gas generator; require the use of larger filters/converters; decrease the operational lifespan of the filter/converter; and/or increase the length of time needed to sanitize the PAP equipment (e.g., by increasing the amount of time needed to remove or convert the larger amount of sanitizing gas to a breathable gas).

One example of a self-sanitizing PAP system consistent with the present disclosure may solve one or more of these problems by integrating a sanitizing gas diffuser in the water reservoir. The sanitizing gas diffuser may be located underneath the water level, thereby improving the distribution of the sanitizing gas into the water. Improving the distribution of the sanitizing gas into the water also allows for the base of the reservoir (i.e., the portion which is typically covered by the water) to also be sanitized. In addition, the pressure of the sanitizing gas may be reduced, thereby reducing the likelihood of a sanitizing gas leak. Moreover, the reduced sanitizing gas pressure may result in a reduction in the amount of sanitizing gas necessary, thereby allowing for a smaller sanitizing gas generator, smaller filter/converter, and/or increased operational lifespan of the filter/converter. Finally, the improved sanitizing gas distribution in the humidifier may reduce the amount of time required to sanitize the PAP equipment.

A further benefit of one or more examples of a self-sanitizing PAP system consistent with the present disclosure is that the sanitizing gas may be introduced at more than one location within the PAP equipment. Additionally (or alternatively), the sanitizing gas may be introduced at the furthest upstream portion of the PAP equipment to be sanitized, and the sanitizing gas may flow substantially only downstream through the PAP equipment (e.g., substantially only downstream from the PAP base unit into the hose and/or mask). This reduces the pressure necessary to ensure that the sanitizing gas comes into contact with all the portions of the PAP equipment to be sanitized. Reducing the pressure also allows for a smaller and/or quieter sanitizing gas generator and/or fan.

As noted above, some of the known systems for sanitizing PAP equipment introduce the sanitizing gas into the PAP equipment through a connector disposed between the hose and the PAP base unit. While these connectors are generally effective, they do require a user to modify the PAP equipment. This can cause confusion for some users. Moreover, the connector units introduce another possible point for the leakage of pressurized air and/or sanitizing gas. One example of a self-sanitizing PAP system consistent with the present disclosure may solve these problems by eliminating the need for the connector unit entirely.

Although the technologies described herein can be used with many gases, the present disclosure focuses on the use of ozone gas as a sanitizing and disinfecting gas. This is because ozone ($O_3$) gas is an effective sanitizer, yet is relatively safe for consumer use. Because of its strong oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Yet naturally over time and/or as it oxidizes contaminants, ozone may be chemically reduced to oxygen ($O_2$), which is safe for human consumption and for release into the environment. Ozone is also relatively easy to generate on site (eliminating the need for a storage tank) and leaves little or no chemical residue. For those and other reasons, ozone has been identified as a safe and effective sanitizing and disinfecting gas for use in the present disclosure. It should be understood, however, that the technologies described herein are not limited to the use of ozone, and may be employed with a wide variety of sanitizing gases known in the art.

Also for the sake of illustration, the present disclosure describes example embodiments in which the technologies described herein utilize ozone gas to sanitize a base tray, bottom channel, water reservoir and/or mist channel of a humidifier. Such examples are for the sake of illustration only, and that the technologies described herein may be used to sanitize any or all components of any suitable type of humidifier. Moreover, the technologies described herein are applicable to applications other than the sanitization of humidifiers.

With the foregoing in mind, and by way of a general overview, the present disclosure generally relates to self-sanitizing positive airway pressure (PAP) systems. The self-sanitizing PAP systems may include a PAP delivery system comprising a hose and a PAP mask, a positive pressure supply system configured to generate a flow of pressurized air which is delivered to a user through the hose to the PAP mask of the PAP delivery system, a sanitizing system configured to sanitize one or more components of the self-sanitizing PAP system, and a PAP base unit housing, wherein one or more components of the positive pressure supply system and the sanitizing system are disposed at least partially within the PAP base unit housing. The self-sanitizing PAP system may optionally include at least one fluid transfer device and the sanitizing system may include a sanitizing gas generator configured to generate a flow of sanitizing gas, wherein the sanitizing gas generator and the fluid transfer device are at least partially disposed within the PAP base unit. The self-sanitizing PAP system may optionally include one or more controllers configured to regulate PAP operations of the positive pressure supply system and sanitization operations of the sanitizing system. The controller(s) may be disposed at least partially within the PAP base unit housing. In at least one example, the controller(s) may be configured to prevent simultaneous operation of PAP operations and sanitization operations. In another example, the controller(s) may be configured to prevent PAP operations in response to an amount of the sanitizing gas within a portion of the self-sanitizing PAP system exceeding a threshold value. The sanitizing system may include at least one sanitizing gas filter or converter configured to absorb the sanitizing gas or convert the sanitizing gas into an inert substance. The controller(s) may be configured to prevent sanitization operations upon in response, at least in part, to a signal from a sensor associated with the sanitizing gas filter or converter.

Turning to FIG. 1, an exemplary schematic view of a self-sanitizing PAP system 100 is generally illustrated. The self-sanitizing PAP system 100 includes at least one positive pressure supply system 102, PAP delivery system 104, sanitizing system 106 configured to sanitize one or more components of the self-sanitizing PAP system 100, and fans, pumps, compressors, blowers, or the like 107 (hereinafter collectively referred to as fluid transfer device 107 for convenience). One or more of the fluid transfer devices 107 may be part of the positive pressure supply system 102 and/or the sanitizing system 106 as described herein. One or more components of the positive pressure supply system 102 and the sanitizing system 106 may be disposed at least partially within a PAP base unit housing 108 as described herein.

During normal PAP operation, the positive pressure supply system 102 generates a flow of pressurized air which is delivered to a user through a hose 110 to a PAP mask 112 of the PAP delivery system 104. The positive pressure supply system 102 may include any type of positive airway pressure device configured to deliver air through the hose 110 and PAP mask 112 to the user's nose and/or mouth. Non-limiting examples of positive pressure supply systems 102 consistent with the present disclosure include Continuous Positive Airways Pressure (CPAP) systems (which apply a substantially constant positive pressure of air to the user), Auto PAP (APAP) systems (which modify the positive pressure level applied during the night for the presence or absence of sleep-induced respiratory disorders), Bi-Level (BiPAP) systems (which use one pressure during inspiration and a lower pressure during expiration), and Adaptive-Servo Ventilation (ASV) systems (which continuously monitor the patient's breathing pattern). The positive pressure supply system 102 may be configured to generate a positive pressure within the hose 110 and/or the PAP mask 112 in the range of about 4 to about 30 $cmH_2O$, for example, in the range of about 6 to about 20 $cmH_2O$.

The hose 110 and PAP mask 112 may include any PAP hose or PAP mask known to those skilled in the art. For example, the hose 110 may include any flexible hose configured to be fluidly coupled to the positive pressure supply system 102 and to the PAP mask 112. The hose 110 may include first and/or second hose connectors 111, 114 that are each configured to be removably fluidly coupled to a PAP base connector 116 and PAP mask connector 118, respectively. By way of a non-limiting example, the first and/or second hose connectors 111, 114 may form a seal with the PAP base connector 116 and/or PAP mask connector 118, respectively, which is sufficient to substantially prevent leakage of air in the normal operation pressure range of the positive pressure supply system 102.

As may be appreciated, the PAP base unit housing 108 may be used with any type of PAP mask 112 and hose 110 based on an individual user's medical needs and/or preferences. To allow users to select between different hoses 110 and/or PAP masks 112, the PAP industry has created standard connections for the PAP base unit housing 108, the hose 110, and the PAP mask 112. In particular, the PAP base connector 116, the PAP mask connector 118, and the first and second hose connectors 111, 114 may conform to a PAP industry standardized design. For example, the first and second hose connectors 111, 114 may define a cavity having a standard diameter opening configured to receive at least a portion of the PAP base connector 116 and/or the PAP mask connector 118, respectively. The PAP base connector 116 and/or the PAP mask connector 118 may therefore have an outer diameter configured to be received inside of the first and second connectors 111, 114. The outer diameter of the PAP base connector 116 and/or the PAP mask connector 118 may substantially correspond to the inner diameter of the cavities of the first and second hose connectors 111, 114. In some examples, the outer surface of PAP base connector 116 and/or the PAP mask connector 118 and/or the inner surface of the first and/or second hose connectors 111, 114 may have a tapered configuration. For example, the outer surface of PAP base connector 116 and/or the PAP mask connector 118 and the inner surface of the first and/or second hose connectors 111, 114 may form a Morse taper (e.g., an interference connection/fit).

As noted herein, the first and second hose connectors 111, 114 (as well as the PAP base connector 116 and/or the PAP mask connector 118) may have an industry-set standard diameter. The industry-set diameter for PAP systems is 22 mm. The flexible tubing of the hose 110 may have a standard diameter of 19 mm; however, there are some PAP systems which use a 15 mm diameter tube. Regardless of the diameter of the tubing of hose 110, in embodiments the first and second hose connectors 111, 114 may have a 22 mm nominal diameter.

The first and second connectors 111, 114 may be made from a resiliently deformable material such as, but not limited natural or synthetic rubber, silicone, or the like, configured to form a seal with the PAP base connector 116 and the PAP mask connector 118. The PAP base connector 116 and/or the PAP mask connector 118 may be made from a more rigid material than the first and second hose connectors 111, 114. For example, the PAP base connector 116 and/or the PAP mask connector 118 may be constructed from silicone, polypropylene, or the like, which has a higher rigidity than the material of the first and second hose connectors 111, 114.

Operation of the positive pressure supply system 102 and/or the sanitizing system 106 may be regulated by one or more controllers 120. In particular, the controller 120 may be configured to adjust one or more PAP operations. The controller 120 may also be configured to adjust one or more sanitization operations. As used herein, "PAP operations" refer to operations performed by the pressure supply system 102 in connection with the delivery of air to the PAP delivery system 104 (e.g., but not limited to, air flow rates, pressures, delivery of supplemental oxygen, filtering, humidification, combinations thereof, and the like). In contrast, the term "sanitization operations" generally refers to operations performed by sanitizing system 106 in connection with the sanitization of one or more components of the self-sanitizing PAP system 100. Non-limiting examples of sanitization operations include operation of pump/fan, operation of sanitizing gas generator, filter detection operations (discussed below), combinations thereof, and the like. While a single controller 120 is shown controlling both the positive pressure supply system 102 and the sanitizing system 106, it should be appreciated that the positive pressure supply system 102 and the sanitizing system 106 may have separate and/or distinct controllers.

Whether the self-sanitizing PAP system 100 has a single controller or multiple controllers, the controller(s) 120 of the self-sanitizing PAP system 100 are able control all aspects of the pressure supply system 102 and the sanitizing system 106, and is therefore better able to ensure safe operation of the self-sanitizing PAP system 100 compared to know sanitizing systems. Thus, in the event of an unsafe condition, the controller 120 can adjust one or more parameters of the pressure supply system 102 and/or the sanitizing system 106. For example, the controller 120 may be configured to ensure that the sanitizing system 106 does not operate at the same time as the pressure supply system 102. Likewise, the controller 120 may be configured to ensure that the pressure supply system 102 does not operate at the same time as the sanitizing system 106. The controller 120 may also be configured to detect an unsafe condition (e.g., based on one or more sensors 124 described herein), and then adjust one or more parameters of the pressure supply system 102 and/or the sanitizing system 106.

The self-sanitizing PAP system 100 may optionally include one or more user interfaces 122, which may include one or more input/output devices. The user interface 122 is generally configured to enable a user to initiate the performance of PAP operations and/or sanitization operations by the self-sanitizing PAP system 100. In embodiments, user interface 122 may include one or more control surfaces, buttons, switches, combinations thereof, and the like, which enable a user to initiate and/or cancel the performance of a PAP operation or a sanitization operation. In those or other embodiments, controller 120 may be programmable, e.g., via user interface 122 or in another manner (e.g., a wired or wireless communication interface), to enable a user to schedule the performance of PAP and/or sanitization operations by the self-sanitizing PAP system 100. In such instances, controller 120 and/or user interface 122 may include a timer that monitors the length of performance of a PAP and/or sanitization operation. When such a timer is used, user interface 122 may include a display for indicating a remaining time for a sanitization and/or PAP operation to a user. Of course, the display is not limited only to indicating the remaining time for such operations, and may be utilized to indicate any suitable information to a user. For example, the user interface 122 may generate a visual, audio, and/or tactile notification to the user indicative of an unsafe operation condition, error message, maintenance message, combinations thereof, or the like.

The self-sanitizing PAP system 100 may optionally include one or more sensors 124. In general, sensor(s) 124 are configured to monitor characteristics of the self-sanitizing PAP system 100 to ensure safe performance of the PAP and/or sanitization operations. For example, the sensor(s) 124 may include a sensor configured to detect the pressure of the air delivered to the user, the flow rate of the air delivered to the user, the humidity of the air delivered to the user, the amount of oxygen in the air delivered to the user, that status of an air filter, the level of water in a water reservoir, the status of the sanitizing system 106, the status of a sanitizing gas filter/converter, user's contact sensors, combinations thereof, and the like. While the sensor(s) 124 is/are illustrated at least partially disposed within the PAP base 108, it should be appreciated that the sensor(s) 124 may be located remotely from the PAP base 108.

Figure 2:
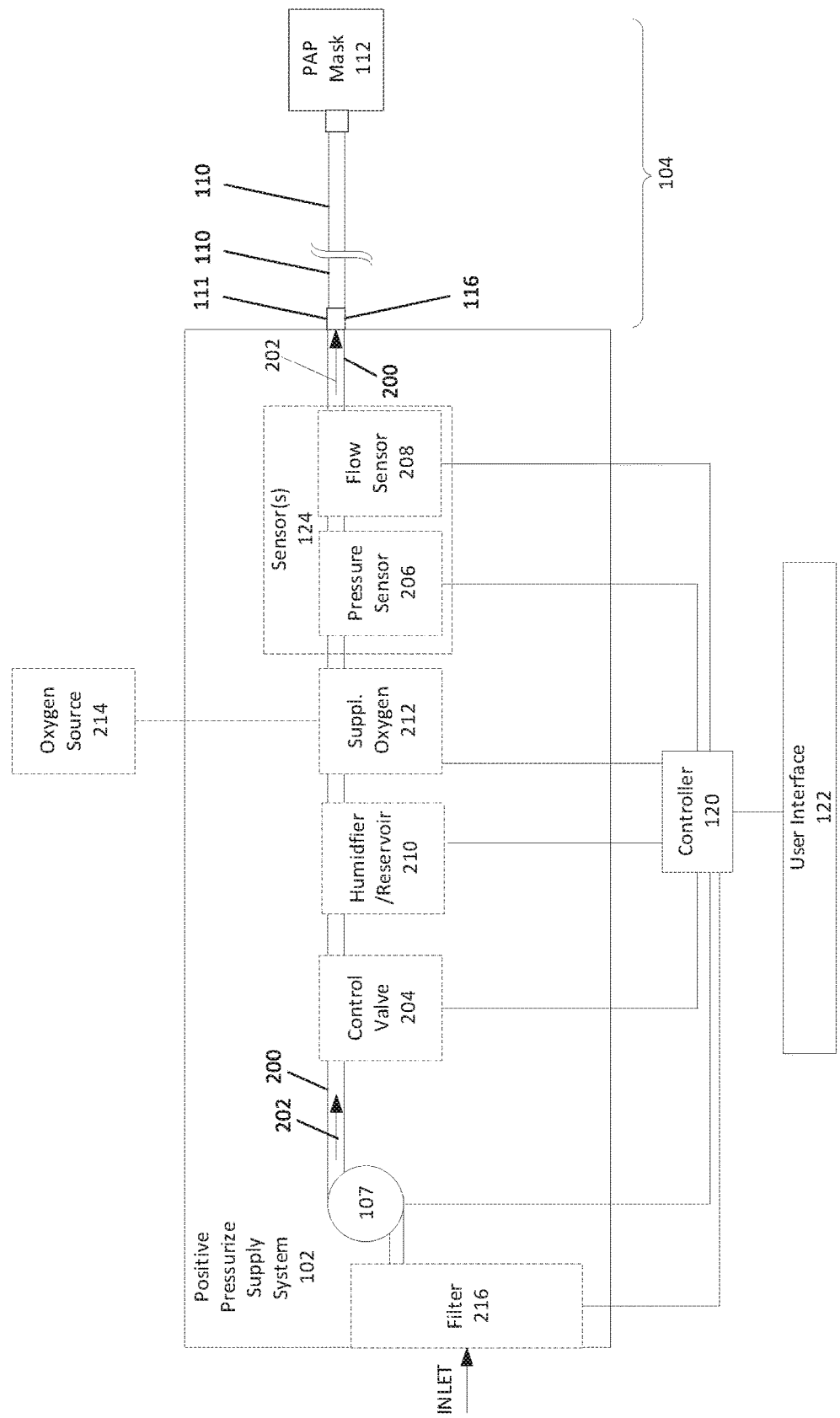
FIG. 2 is schematic view of one example of a positive pressure supply system of FIG. 1 consistent with the present disclosure.

Turning now to FIG. 2, one example of a positive pressure supply system 102 of FIG. 1 is generally illustrated in more detail. The positive pressure supply system 102 may include one or more fluid transfer devices 107 fluidly coupled to at least one positive pressure air conduit 200 configured to generate/provide a flow of pressurized air 202 to the PAP delivery system 104. The positive pressure air conduit 200 may include a PAP base connector 116 disposed at a distal end which is configured to be removably fluidly coupled to the first hose connector 111 of the hose 110. While the fluid transfer device 107 is shown as being part of the positive pressure supply system 102, it should be appreciated that the positive pressure supply system 102 may be part of and/or shared with the sanitizing system 106.

In some examples, the controller 120 may regulate the flow rate and/or pressure of the airflow 202 by regulating the fluid transfer device 107 and/or one more optional control valves 204 based on signals from one or more optional sensors 124 (e.g., but not limited to, pressure sensors 206 and/or flow sensors 208). For example, the controller 120 may to adjust the flow rate and/or pressure of the airflow 202 by regulating the fluid transfer device 107 (e.g., by adjusting the voltage to the fluid transfer device 107 to change the speed of the fluid transfer device 107). Alternatively (or in addition), the controller 120 may adjust the flow rate and/or pressure of the airflow 202 by regulating the position of the control valve 204. For example, the control valve 204 may be opened to bleed off excessive air generated by the fluid transfer device 107 to the atmosphere and/or may be closed to restrict the flow of air therethrough to reduce the flow rate. It should be apparent that a positive pressure supply system 102 consistent with the present disclosure may utilize any known mechanism for adjusting the flow rate and/or pressure of the airflow 202 provided to the PAP delivery system 104 and ultimately to the user.

The positive pressure supply system 102 may optionally include one or more humidifiers 210. The humidifier 210 may include a water reservoir, and may be configured to increase the moisture level of the airflow 202. While humidified air will generally have a humidity greater than the humidity of the air in the environment surrounding the self-sanitizing PAP system 100, such a characteristic is not required.

The positive pressure supply system 102 may optionally include a supplemental oxygen system 212. The supplemental oxygen system 212 may configured to increase the amount of oxygen in the airflow 202 and may optionally include signals from one or more sensors 124 (e.g., an oxygen sensor) configured to generate a signal representative of the amount of oxygen in the airflow 202 to the PAP delivery system 104. The supplemental oxygen system 212 may be fluidly coupled to an oxygen source 214. The oxygen source 214 may include an oxygen tank and/or an oxygen generator. The supplemental oxygen system 212 may include an adjustable valve regulated by the controller 120 to adjust the flow rate of oxygen into the airflow 202, e.g., based on the signal from the oxygen sensor. Alternatively, the controller 120 may regulate the oxygen generator (e.g., based on the signal from the oxygen sensor) to adjust the flow rate of oxygen into the airflow 202.

Airborne debris may be prevented from entering and/or removed from the airflow 202 by way of one or more filters 216. The filter 216 may be configured to remove odors, dust particles, allergens, environmental contaminants, and the like. In some examples, the filter may include a high-efficiency particulate air (HEPA), a charcoal filter, an N95 filter, combinations thereof, and the like. While the filter 216 is shown proximate to the inlet of the fluid transfer device 107, it should be appreciated that one or more filters 216 may be located anywhere in the self-sanitizing PAP system 100. The controller 120 may be configured to monitor the status of the filter 216, for example, to ensure that the filter 216 is present, determine when the filter 216 needs to be replaced, and/or determine if the quality of the inlet air is sufficient for use during PAP operations (e.g., determine if the inlet air has too much debris/contaminants, too little oxygen, etc.).

At least some of the components of the positive pressure supply system 102 are integral with the PAP base unit housing 108 of the self-sanitizing PAP system 100. For example, one or more of the fluid transfer devices 107, PAP base connector 116, controllers 120, user interfaces 122, sensors 124, positive pressure air conduit 200, control valves 204, humidifiers and/or water reservoirs 210, supplemental oxygen 212, filters 216, combinations thereof, and the like may be sized and configured to fit/disposed at least partially within and/or integral with the PAP base unit housing 108 of the self-sanitizing PAP system 100. In at least one example, the fluid transfer devices 107, PAP base connector 116, controllers 120, user interfaces 122, and/or positive pressure air conduit 200 are integral with the PAP base unit housing 108 of the self-sanitizing PAP system 100. According to another example, the fluid transfer devices 107, PAP base connector 116, controllers 120, user interfaces 122, positive pressure air conduit 200, and/or humidifiers/water reservoirs 210 are integral with the PAP base unit housing 108 of the self-sanitizing PAP system 100.

As should be evident from the above, the positive pressure supply system 102 shown in FIG. 2 is merely for illustrative purposes only. The positive pressure supply system 102 of present disclosure may include any known system for generating a positive airflow to the user, and should not be limited to the particulars shown and described herein unless specifically claimed as such.

Figure 3:
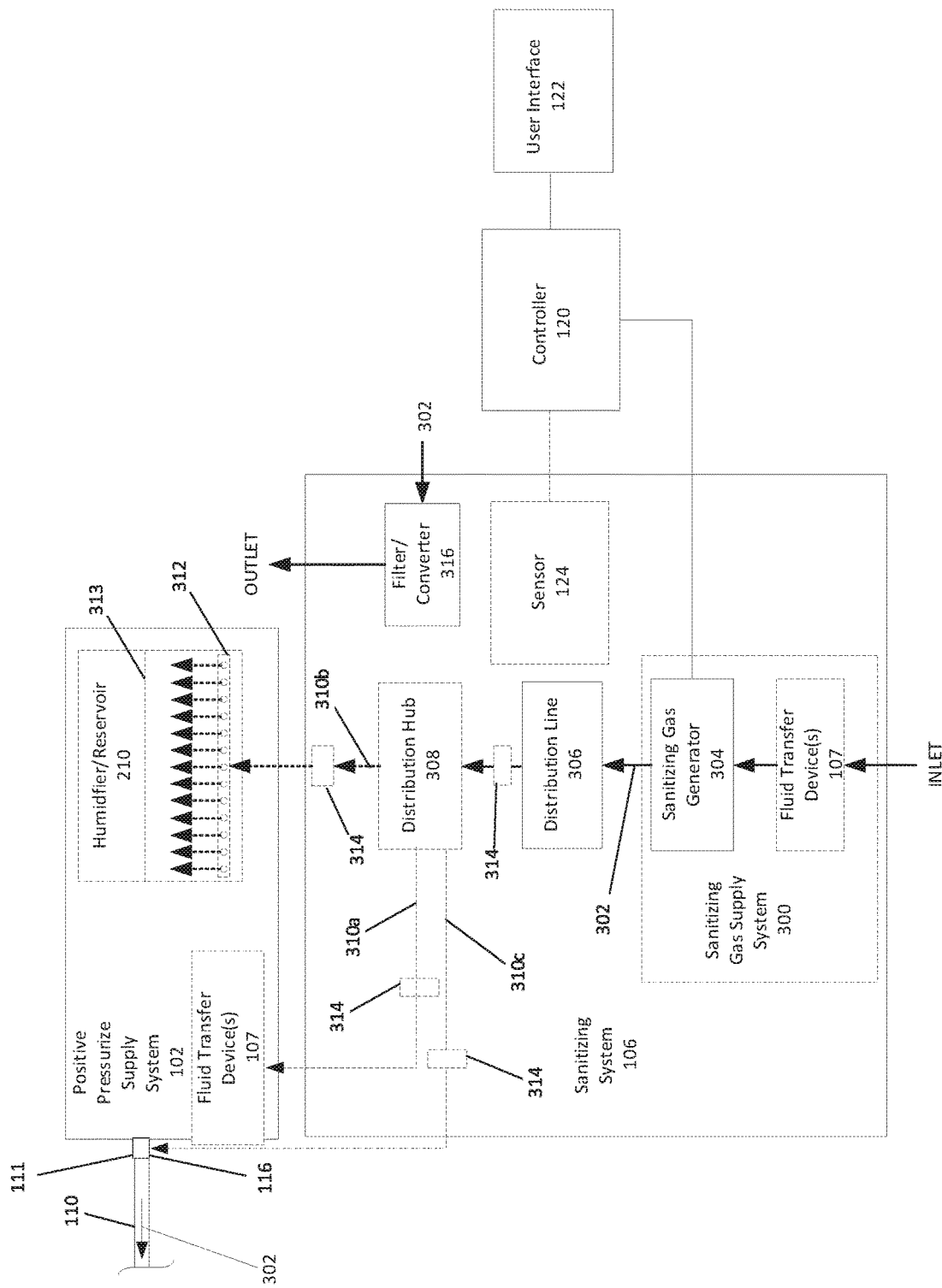
FIG. 3 is schematic view of one example of a sanitizing system of FIG. 1 consistent with the present disclosure.

With reference to FIG. 3, one example of a sanitizing system 106 of FIG. 1 is generally illustrated in more detail. The sanitizing system 106 includes sanitizing gas supply system 300 configured to generate a flow of sanitizing gas 302 and distribute the flow of sanitizing gas 302 to at least a portion of the PAP delivery system 104 and/or the positive pressure supply system 102. In some examples, the sanitizing system 106 may be configured to selectively distribute the flow of sanitizing gas 302 based on one or parameters (e.g., but not limited to, user input, predefined or calculated schedules, selected events, input from sensor(s) 124, combinations thereof, and the like). The sanitizing system 106 may be regulated by, for example, the controller 120 and/or user interface 122. It should be appreciated that the controller 120 and/or user interface 122 may be the same controller and/or user interface used to regulate the positive pressure supply system 102 or may be a different/separate controller and/or user interface.

Without limitation, in some embodiments the sensors 124 include sanitizing gas sensors that are configured to sense the presence and/or concentration of sanitizing gas within at least a portion of the positive pressure supply system 102 and/or PAP delivery system 104. The sanitizing gas sensors may function to sense the presence of sanitizing gas and to output a gas sensor signal to controller 120, wherein the gas sensor signal is indicative of the presence and/or concentration of the sanitizing gas in one a respective component of at least a portion of the positive pressure supply system 102 and/or PAP delivery system 104. In such instances controller 120 may determine the presence and/or concentration of sanitizing gas within at least a portion of the positive pressure supply system 102 and/or PAP delivery system 104 based at least in part on the gas sensor signal. In embodiments, controller 120 is configured to prevent and/or disable performance of PAP operations when it is determined that sanitizing gas is present within at least a portion of the positive pressure supply system 102 and/or PAP delivery system 104. Alternatively, controller 120 may determine a concentration of sanitizing gas within at least a portion of the positive pressure supply system 102 and/or PAP delivery system 104 and compare the determined concentration to a threshold concentration of sanitizing gas. When the determined concentration is greater than or equal to the threshold concentration, controller 120 may disable or prevent performance of a PAP operation. When the determined concentration is below the threshold concentration, however, controller 120 may permit the performance of a PAP operation.

The sanitizing gas supply system 300 includes at least one sanitizing gas generator 304. For example, sanitizing gas generator 304 may be an ozone generator that is configured to generate ozone gas at least in part from inlet air, e.g., provided by fluid transfer device 107. Any suitable ozone gas generator may be used for that purpose, provided it can generate ozone at least in part from inlet air. Without limitation, in embodiments sanitizing gas generator 304 is an ozone generator that is sized and configured to fit within the PAP base unit housing 108 of the self-sanitizing PAP system 100. In other words, in some embodiments sanitizing gas generator 304 (and/or sanitizing gas supply system 109) is integral with the PAP base unit housing 108 of the self-sanitizing PAP system 100. For example, the sanitizing gas generator 304, the fluid transfer devices 107, PAP base connector 116, controllers 120, user interfaces 122, and positive pressure air conduit 200 are integral with the PAP base unit housing 108 of the self-sanitizing PAP system 100. According to another example, the sanitizing gas generator 304, the fluid transfer devices 107, PAP base connector 116, controllers 120, user interfaces 122, and positive pressure air conduit 200, and/or humidifiers/water reservoirs 210 are integral with the PAP base unit housing 108 of the self-sanitizing PAP system 100.

The sanitizing system 106 (e.g., the sanitizing gas supply system 300) may optionally include one or more fluid transfer devices 107. For example, the fluid transfer device 107 may be separate from a fluid transfer device 107 associated with the positive pressure supply system 102. Alternatively, the fluid transfer device 107 may work in conjunction with the fluid transfer device 107 associated with the positive pressure supply system 102. According to yet another example, the positive pressure supply system 102 and the sanitizing system 106 may commonly use (share) one or more fluid transfer devices 107. One or more fluid transfer devices 107 associated with the sanitizing system 106 may be sized and configured to fit/disposed at least partially within and/or integral with the PAP base unit housing 108 of the self-sanitizing PAP system 100. Alternatively, or in addition, one or more fluid transfer devices 107 associated with the sanitizing system 106 may be located remotely from (i.e., not within) the PAP base unit housing 108 of the self-sanitizing PAP system 100.

The sanitizing system 106 includes one or more distribution lines 306 that are fluidly coupled to sanitizing gas generator 304, and which is fluidly coupled to at least a portion of one or more components of the positive pressure supply system 102 and/or PAP delivery system 104. For example, the distribution line 306 may be fluidly (and in some instances, directly) permanently and/or removably coupled to the fluid transfer devices 107 associated with the positive pressure supply system 102, positive pressure air conduit 200, reservoir 210, or a combination of two or more thereof. Alternatively (or in addition), the distribution line 306 may be fluidly (and in some instances, directly) permanently and/or removably coupled to at least a portion of the hose 110 and/or mask 112 of the PAP delivery system 104.

The sanitizing system 106 may optionally include a distribution hub 308 that is fluidly coupled to the distribution line 115 (e.g., a distal end of distribution line 115). In general, distribution hub 308 is configured to distribute a flow of sanitizing gas 302 (e.g., ozone) from distribution line 306 to one or more components of the positive pressure supply system 102 and/or PAP delivery system 104. In that regard, distribution hub 308 may include or be fluidly coupled to one or more channels 310a-310c, which in turn are fluidly coupled to one or more components of the positive pressure supply system 102 and/or PAP delivery system 104. The distribution hub 308 and at least a portion of channels 310a-310c may be are integral with the PAP base unit housing 108 of the self-sanitizing PAP system 100. For example, the distribution hub 308 and at least a portion of channels 310a-310c, the sanitizing gas generator 304, the fluid transfer devices 107, PAP base connector 116, controllers 120, user interfaces 122, and positive pressure air conduit 200 are integral with the PAP base unit housing 108 of the self-sanitizing PAP system 100. According to another example, the distribution hub 308 and at least a portion of channels 310a-310c, the sanitizing gas generator 304, the fluid transfer devices 107, PAP base connector 116, controllers 120, user interfaces 122, positive pressure air conduit 200, and/or humidifiers/water reservoirs 210 are integral with the PAP base unit housing 108 of the self-sanitizing PAP system 100.

The distribution hub 308 may include or be fluidly coupled to a first channel 310a, which is fluidly coupled to positive pressure supply system 102 (e.g., but not limited to, the fluid transfer devices 107 associated with the positive pressure supply system 102, the positive pressure air conduit 200, the PAP base connector 116, or a combination of two or more thereof). The distribution hub 308 may additionally (or alternatively) include or be fluidly coupled to a second distribution channel 310b, which is fluidly coupled to humidifier 210. For example, the second distribution channel 310b may include one or more diffusers 312, which may be at least partially disposed within or exposed to the liquid 313 of the reservoir associated with the humidifier 210. The diffuser 312 may be configured to distribute sanitizing gas within the humidifier 210 during a sanitization operation. The distribution hub 308 may also include or be fluidly coupled to a third distribution channel 310c, which is fluidly coupled the PAP delivery system 104. For example, the third distribution channel 310c may be removably fluidly coupled to the first hose connector 111.

One or more valves 314 may be coupled to one or more of the distribution channels 310a-310c and/or distribution line 306. Valves 314 may be configured to adjust a flow of sanitizing gas to each channel 310a-c and/or through distribution line 306 to which the distribution hub 308 is fluidly coupled and, thus, to the components of the positive pressure supply system 102 and/or PAP delivery system 104 that are attached to each respective distribution channel. For example, one or more of the valves 314 may be regulated by the controller 120. In embodiments, distribution hub 308 is preconfigured to supply a pre-determined flow of sanitizing gas 302 to each of the distribution channels 310a-c to which it is fluidly coupled. One or more of the valves 314 may also be configured to prevent the back flow of liquid and/or gas into distribution hub 308 from respective components of positive pressure supply system 102 and/or PAP delivery system 104. In such an example, the valves 314 may include check valves or the like. One or more of the valves 314 may be integral with the PAP base unit housing 108 of the self-sanitizing PAP system 100.

The sanitizing system 106 also includes at least one sanitizing gas filter/converter 316. The sanitizing gas filter/converter 316 is generally configured to absorb the sanitizing gas 302 and/or to convert the sanitizing gas 302 to another composition (e.g., an inert substance and/or a breathable gas) that is safe for discharge into the environment. Non-limiting examples of suitable filters that may be used for such a purpose include magnesium oxide filters and activated carbon filters. In embodiments, the sanitizing gas filter/converter 316 is or includes magnesium oxide, and is configured to convert sanitizing gas 302 (e.g., ozone) to a breathable gas (e.g. oxygen).

The sanitizing gas filter/converter 316 is positioned proximate the outlet 318 of the sanitizing system 106. In some examples, the sanitizing gas filter/converter 316 is disposed within the PAP base unit housing 108. Alternatively (or in addition), the sanitizing gas filter/converter 316 is disposed remotely from (e.g., separate) the PAP base unit housing 108.

The controller 120 may be configured to prevent sanitization operations and/or prevent PAP operations in the event that the sanitizing gas filter/converter 316 is not fluidly coupled to the sanitizing system 106 and/or is not operating properly (e.g., due to improper installation, expired service life, damage, etc.). With that in mind, sensors 124 may include a filter detection sensor that is configured to monitor one or more parameters associated with the sanitizing gas filter/converter 316. For example, sensors 124 may monitor the position of the sanitizing gas filter/converter 316 and to output a filter detection signal to controller 120 indicative of whether the sanitizing gas filter/converter 316 is properly installed/coupled to the sanitizing gas flow 302. Any suitable filter detection sensor may be used. For example, a filter detection sensor in the form of or including an optical sensor for detection a position of the filter may be used. Alternatively (or additionally), the filter detection sensor may include or be in the form of a latch, button, switch, or the like, which is pressed, depressed, or the like when the filter is in the closed position, and is released (i.e., not pressed or depressed) when the filter is in the open position. Still further, the filter detection sensor may include a conductive pad that is configured to electrical couple with a corresponding conductive pad on the filter when the filter is in the closed position—resulting in a detectable change in electrical properties, e.g., conductivity, resistance, voltage, etc. that can be conveyed in a filter detection signal.

The sensor 124 may also be configured to determine if the sanitizing gas filter/converter 316 is operating properly. For example, the sensor 124 may monitor the gas exiting from the sanitizing gas filter/converter 316 and determine if the amount of sanitizing gas exceeds a threshold. This may be done by directly monitoring for the sanitizing gas or monitoring the amount of the conversion gas (e.g., oxygen). Alternatively (or in addition), the filter 124 may determine the remaining useful life of the sanitizing gas filter/converter 316. This may be done using a timer/count-down which decrements once the sanitizing gas filter/converter 316 is installed. The decrement may be based on the operational use of the sanitizing gas filter/converter 316 and/or based on installation. In any event, the controller 120 may determine if the sanitizing gas filter/converter 316 is in proper operational condition, and when it is determined that sanitizing gas filter/converter 316 is not in proper operational condition, controller 120 may prevent or disable operation of one or more components of sanitizing system 106 and/or positive pressure supply system 102 (e.g., fluid transfer devices 107 and/or sanitizing gas supply system 300). Without limitation, controller 120 may prevent and/or disable operation of sanitizing gas generator 304 when sanitizing gas filter/converter 316 is not installed.

Sensors 124 may also include one or more sanitizing gas sensors. When used, the sanitizing gas sensors may be configured to sense the presence and/or concentration of sanitizing gas within one or more components of self-sanitizing PAP system 100. In that regard, sanitizing gas sensors may be used to detect the presence and/or concentration of sanitizing gas within the positive pressure supply system 102 (e.g., but not limited to, positive pressure air conduit 200, fluid transfer devices 107, PAP base connector 116, humidifier 210, or a combination thereof), PAP delivery system 104 (e.g., but not limited to, hose 110 and/or mask 112), and/or the sanitizing system 106 (e.g., but not limited to, distribution line 306, distribution hub 308, distribution channels 310a-310c, or a combination thereof). The sanitizing gas sensors may function to sense the presence of sanitizing gas and to output a gas sensor signal to controller 120, wherein the gas sensor signal is indicative of the presence and/or concentration of the sanitizing gas in one a respective component of self-sanitizing PAP system 100. In such instances controller 120 may determine the presence and/or concentration of sanitizing gas within self-sanitizing PAP system 100 based at least in part on the gas sensor signal. In embodiments, controller 120 is configured to prevent and/or disable performance of a PAP operation and/or sanitization operation when it is determined that sanitizing gas is improperly present within self-sanitizing PAP system 100. Alternatively, controller 120 may determine a concentration of sanitizing gas within the self-sanitizing PAP system 100 (or a component thereof) and compare the determined concentration to a threshold concentration of sanitizing gas. When the determined concentration is greater than or equal to the threshold concentration and the self-sanitizing PAP system 100 is performing or requested to perform PAP operations, controller 120 may disable or prevent performance of a PAP operation and/or sanitization operation. When the determined concentration is below the threshold concentration, however, controller 120 may permit the performance of a PAP operation.

Figure 4:
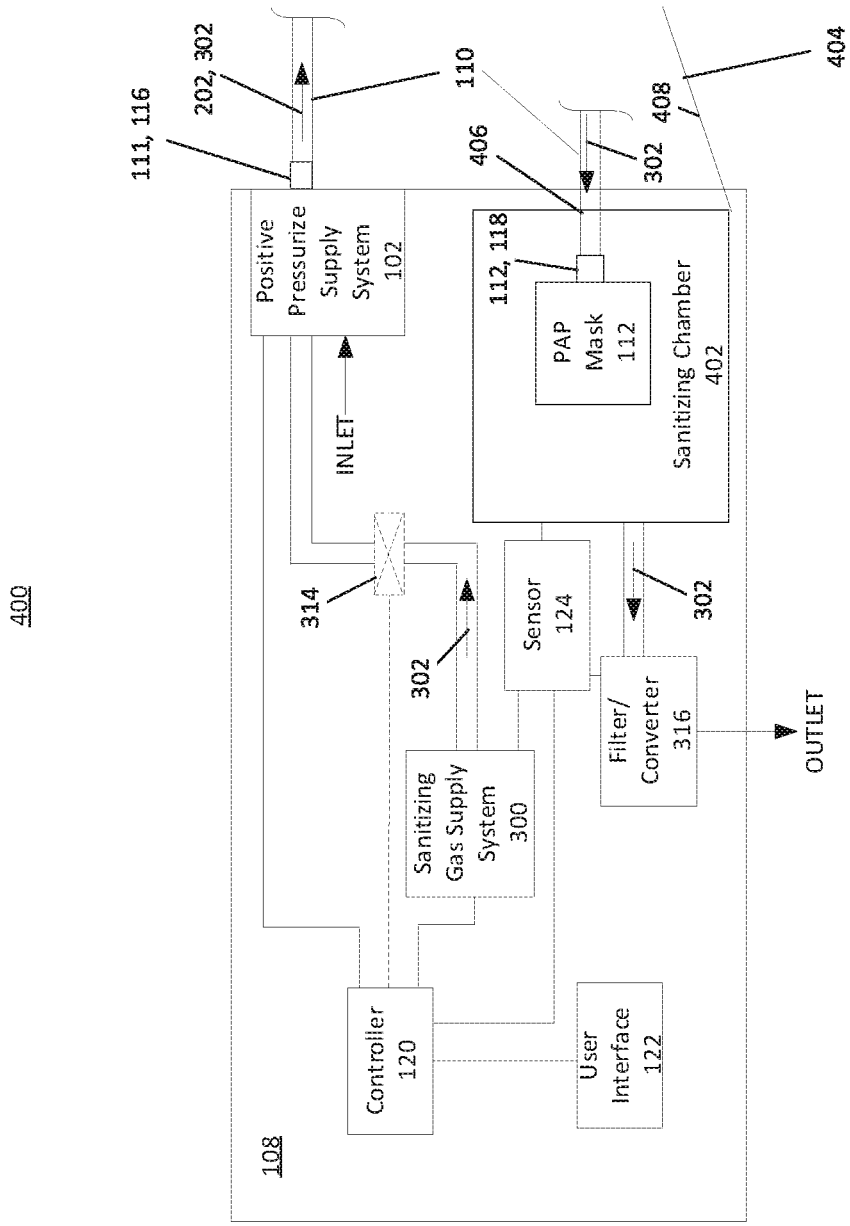
FIG. 4 is schematic view of one example of a positive pressure supply system and sanitizing system of FIG. 1 consistent with the present disclosure.

Turning now to FIG. 4, another example of a self-sanitizing system 400 consistent with FIG. 1 of the present disclosure is generally illustrated. The self-sanitizing system 400 may include a positive pressure supply system 102 including a PAP base connector 116 configured to be fluidly coupled to the first hose connector 111 of the hose 110. The second hose connector 114 may be configured to be fluidly coupled to the PAP mask connector 118 of the PAP mask 112. The sanitizing gas supply system 300 may be configured to generate and provide a flow of sanitizing gas 302 to one or more components of the positive pressure supply system 102. The sanitizing gas 302 may exit the positive pressure supply system 102 and flow through the hose 110 and/or PAP mask 112. The sanitizing gas 302 may therefore be exposed to and therefore sanitize one or more components of the positive pressure supply system 102 and the PAP delivery system 104. One or more valves 314 may be configured to regulate and/or prevent the flow of sanitizing gas 302 into the positive pressure supply system 102 as described herein.

The self-sanitizing system 400 may include one or more sanitizing chambers 402. The sanitizing chamber 402 may be sized and shaped to receive the PAP mask 112 and/or a portion of the hose 110. The sanitizing chamber 402 may include one or more moveable lids 404 to provide access to the interior of the sanitizing chamber 402. The lids 404 is illustrated in the open position to allow the user to place the hose 110 (and optionally the PAP mask 112) into the sanitizing chamber 402. The sanitizing chamber 402 may also optionally include an opening or slot 406 configured to allow the hose 110 to pass into the interior of the sanitizing chamber 402, for example, when the lid 404 is closed. The lid 404 and/or opening 406 may include seals 408 to generally prevent leakage of sanitizing gas 302 from the sanitizing chamber 402 and into the atmosphere. One or more sensors 124 may be provided to monitor whether sanitizing gas 302 is leaking from the sanitizing chamber 402 as described herein. The sanitizing chamber 402 may be integral with the PAP base unit housing 108 of the self-sanitizing PAP system 100. For example, the sanitizing chamber 402, distribution hub 308 and at least a portion of channels 310a-310c, the sanitizing gas generator 304, the fluid transfer devices 107, PAP base connector 116, controllers 120, user interfaces 122, and/or positive pressure air conduit 200 are integral with the PAP base unit housing 108 of the self-sanitizing PAP system 100. According to another example, the sanitizing chamber 402, the distribution hub 308 and at least a portion of channels 310a-310c, the sanitizing gas generator 304, the fluid transfer devices 107, PAP base connector 116, controllers 120, user interfaces 122, positive pressure air conduit 200, and/or humidifiers/water reservoirs 210 are integral with the PAP base unit housing 108 of the self-sanitizing PAP system 100.

The self-sanitizing system 400 may also include one or more sanitizing gas filter/converter(s) 316. The sanitizing gas filter/converter 316 is fluidly coupled to the sanitizing chamber 402 and is configured to receive the sanitizing gas 302 and absorb and/or convert the sanitizing gas 302 as described herein. A sensor 124 may monitor the status of the sanitizing gas filter/converter 316 to ensure proper operation as described herein.

In the illustrated example, the sanitizing chamber 402 and the sanitizing gas filter/converter 316 are at least partially disposed within the PAP base unit housing 108 of the self-sanitizing system 400. As such, the PAP operations of the positive pressure supply system 102 and the sanitization operations of the sanitizing system 106 may all be disposed within the PAP base unit housing 108 of the self-sanitizing system 400. For example, the PAP operations of the positive pressure supply system 102 and the sanitization operations of the sanitizing system 106 may all be disposed within a single, one-piece unit.

Figure 5:
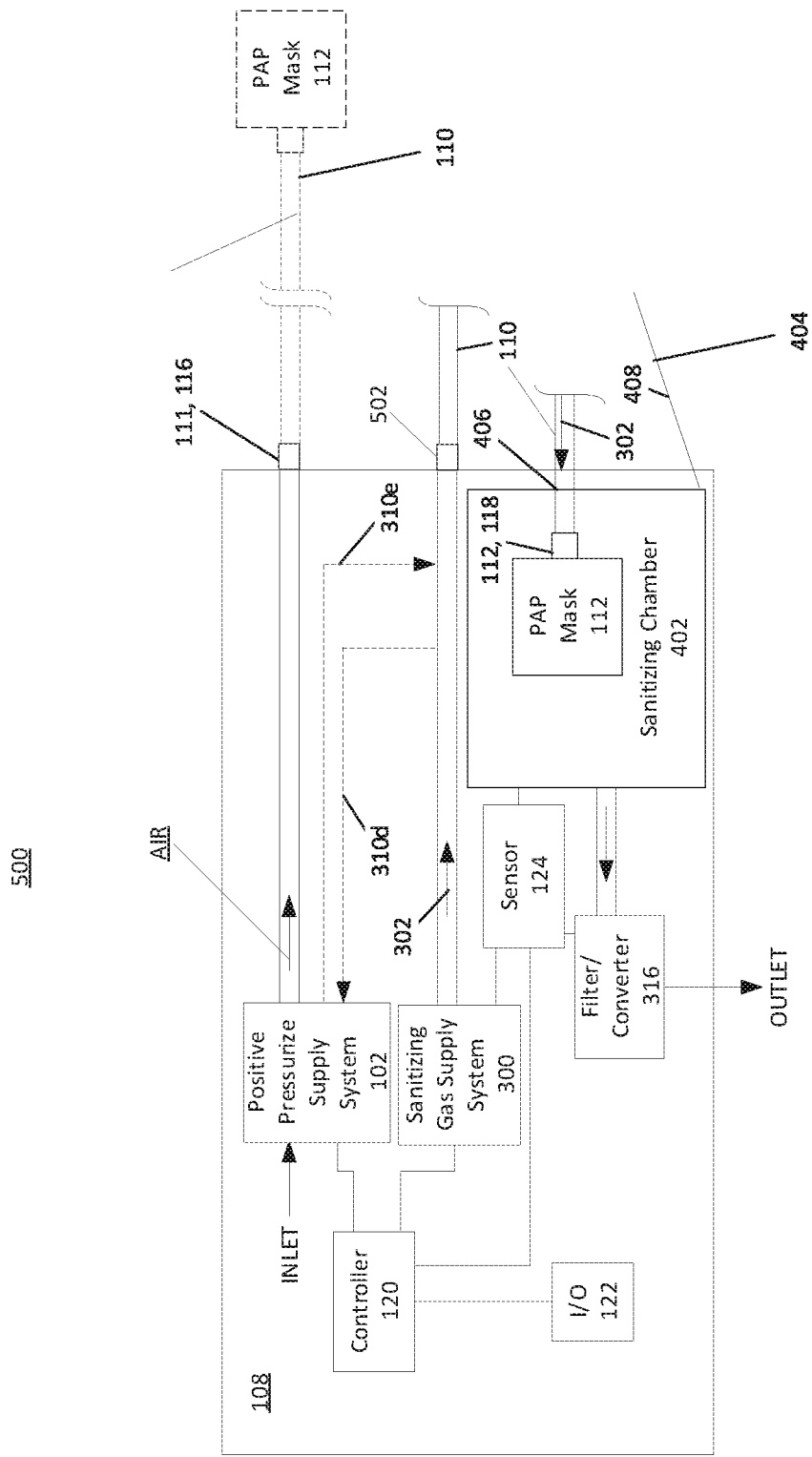
FIG. 5 is schematic view of another example of a positive pressure supply system and sanitizing system of FIG. 1 consistent with the present disclosure.

Turning now to FIG. 5, another example of a self-sanitizing system 500 consistent with FIG. 1 of the present disclosure is generally illustrated. The self-sanitizing system 500 may include one or more sanitizing chambers 402 and one or more sanitizing gas filter/converter 316 as described herein. The self-sanitizing system 500 may also include a positive pressure supply system 102 including a PAP base connector 116 configured to be fluidly coupled to the first hose connector 111 of the hose 110. The second hose connector 114 may be configured to be fluidly coupled to the PAP mask connector 118 of the PAP mask 112. The sanitizing gas supply system 300 may be configured to generate and provide a flow of sanitizing gas 302 to a sanitizing gas outlet/connector 502. The sanitizing gas outlet/connector 502 may be configured to be removably fluidly coupled to the first hose connector 111 of the hose 110. As such, the first hose connector 111 of the hose 110 may couple to the first hose connector 111 of the hose 110 in substantially the same manner as the PAP base connector 116 connects to the first hose connector 111. In at least one example, however, the sanitizing gas outlet/connector 502 may be configured to prevent the first hose connector 111 of the hose 110 from being coupled to the sanitizing gas outlet/connector 502 unless the second end 112 and/or PAP mask 112 are disposed within the sanitizing chamber 402. For example, the self-sanitizing system 500 may include a sensor 124 configured to determine when the lid 408 is closed and/or when the hose 110 and/or the PAP mask 112 is disposed within the sanitizing chambers 402.

The sanitizing gas 302 may therefore flow from the sanitizing gas supply system 300 and through a sanitizing gas outlet/connector 502 (which is separate and distinct from the PAP base connector 116) and into the hose 110 and/or the PAP mask 112, into the sanitizing chamber 402, and to the sanitizing gas filter/converter 316. Optionally, a portion of the sanitizing gas 302 may flow internally within the PAP base unit housing 108 from the sanitizing gas supply system 300, through a supply positive pressure supply system distribution line 310d, to the positive pressure supply system 102, and returning to the sanitizing gas supply system 300 via a return positive pressure supply system distribution line 310e.

In the illustrated example, the sanitizing chamber 402 and the sanitizing gas filter/converter 316 are at least partially disposed within the PAP base unit housing 108 of the self-sanitizing system 500. As such, the PAP operations of the positive pressure supply system 102 and the sanitization operations of the sanitizing system 106 may all be disposed within the PAP base unit housing 108 of the self-sanitizing system 500. For example, the PAP operations of the positive pressure supply system 102 and the sanitization operations of the sanitizing system 106 may all be disposed within single, one-piece unit.

Figure 6:
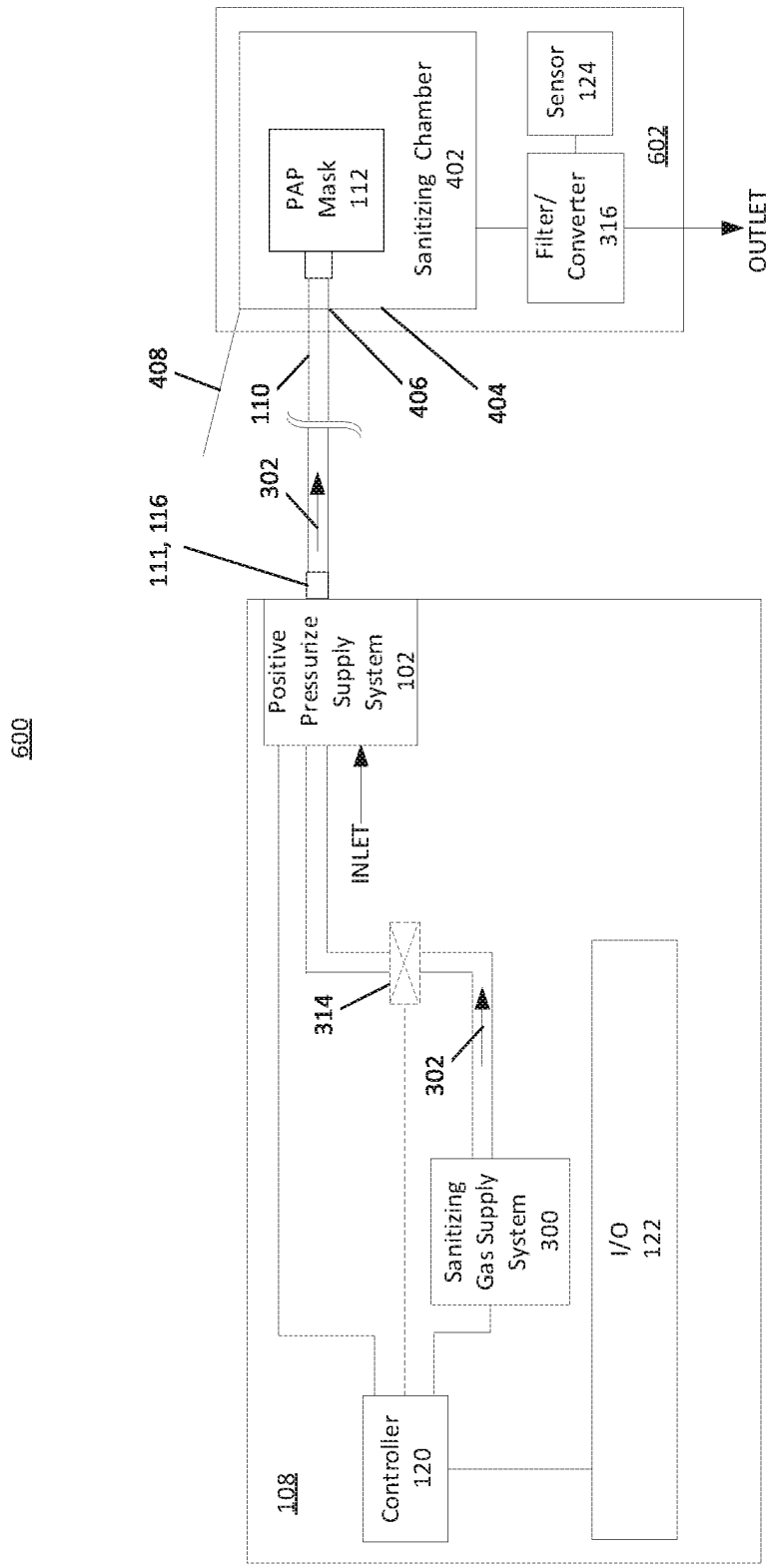
FIG. 6 is schematic view of yet another example of a positive pressure supply system and sanitizing system of FIG. 1 consistent with the present disclosure.

Alternatively, the sanitizing chamber 402 and the sanitizing gas filter/converter 316 may be disposed remotely from the PAP base unit housing 108. With reference to FIG. 6, one example of a self-sanitizing system 600 featuring the sanitizing chamber 402 and the sanitizing gas filter/converter 316 disposed in a separate and distinct sanitizing housing 602 from the PAP base unit housing 108) is generally illustrated. As shown, the first hose connector 111 of the hose 110 may be fluidly coupled to the PAP connector 116. The sanitizing gas supply system 300 may therefore be configured to provide sanitizing gas 302 to one or more components of the sanitizing gas supply system 300 as well as the hose 110 through the PAP connector 116. Alternatively, the first hose connector 111 of the hose 110 may be fluidly coupled to a sanitizing gas outlet/connector 502, for example, as generally illustrated in FIG. 5. In any event, one or more of the sensors 124 (e.g., the sensors 124 disposed within the sanitizing housing 602 and associated with the sanitizing chamber 402 and/or sanitizing gas filter/converter 316) may be configured to wirelessly communicate with the controller 120.

While not shown, the sanitizing housing 602 may include one or more fluid transfer device 107. The fluid transfer device 107 in the sanitizing housing 602 may aid in distributing the sanitizing gas 302 to the sanitizing chamber 402. The fluid transfer device 107 may work in conjunction with a fluid transfer device 107 in the PAP base unit housing 108 (e.g., a fluid transfer device 107 in the PAP base unit housing 108 associated with the pressure supply system 102 and/or the sanitizing system 106 as described herein). Alternatively, the fluid transfer device 107 may work separate and independently from a fluid transfer device 107 in the PAP base unit housing 108 (e.g., a fluid transfer device 107 in the PAP base unit housing 108 associated with the pressure supply system 102 and/or the sanitizing system 106 as described herein).

The controller 120 may be configured to prevent one or more of the sanitization operations unless the hose 110 and/or PAP mask 112 are disposed within and/or sealed to the sanitizing chamber 402. For example, sensor 124 may detect if the hose 110 and/or PAP mask 112 are disposed within and/or sealed to the sanitizing chamber 402, for example, using an optical sensor, contact sensor, or the like.

Figure 7:
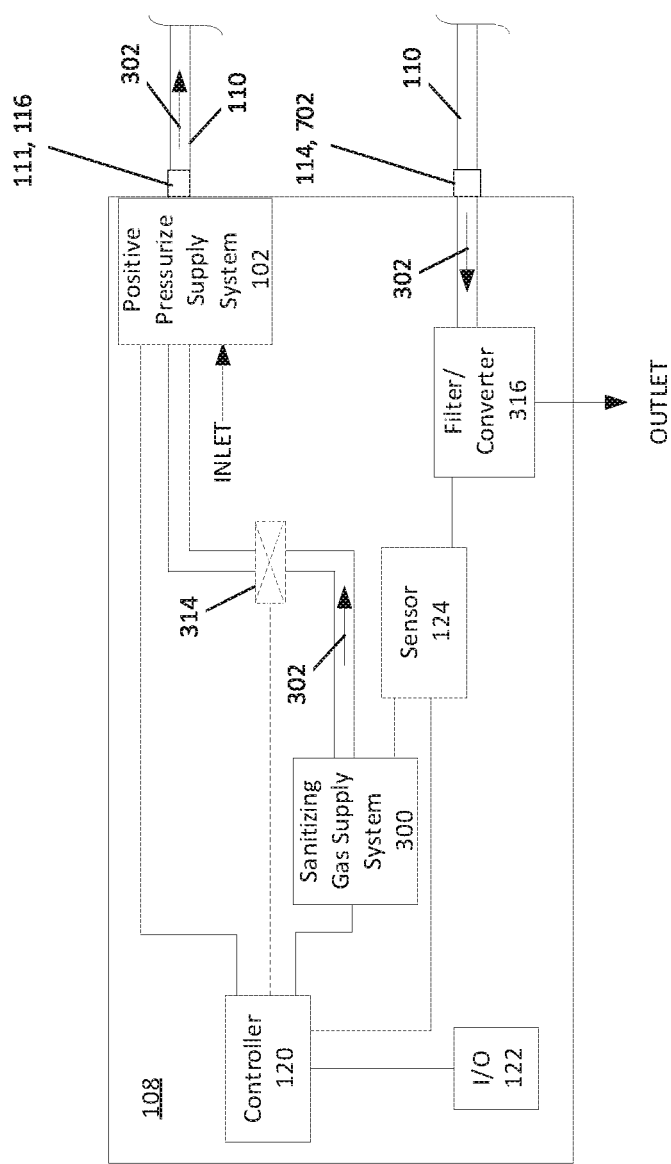
FIG. 7 is schematic view of a further example of a positive pressure supply system and sanitizing system of FIG. 1 consistent with the present disclosure.

Turning now to FIG. 7, a further example of a self-sanitizing system 700 consistent with FIG. 1 of the present disclosure is generally illustrated. The self-sanitizing system 700 of FIG. 7 may be similar to the self-sanitizing system 400 of FIG. 4; however, rather than having a sanitizing chamber 402 disposed within the PAP base unit housing 108, the self-sanitizing system 700 of FIG. 7 may include a sanitizing gas inlet/connector 702 configured to be fluidly coupled to the second hose connector 114 of the hose 110. The sanitizing gas inlet/connector 702 may be fluidly coupled to the sanitizing gas filter/converter 316. As such, the sanitizing gas 302 may flow from the sanitizing gas supply system 300, through one or more components of the positive pressure supply system 102, through the hose 110 and sanitizing gas inlet/connector 702, and to the sanitizing gas filter/converter 316. The sanitizing gas inlet/connector 702 and the sanitizing gas filter/converter 316 at least partially disposed within the PAP base unit housing 108 of the self-sanitizing system 700.

Figure 8:
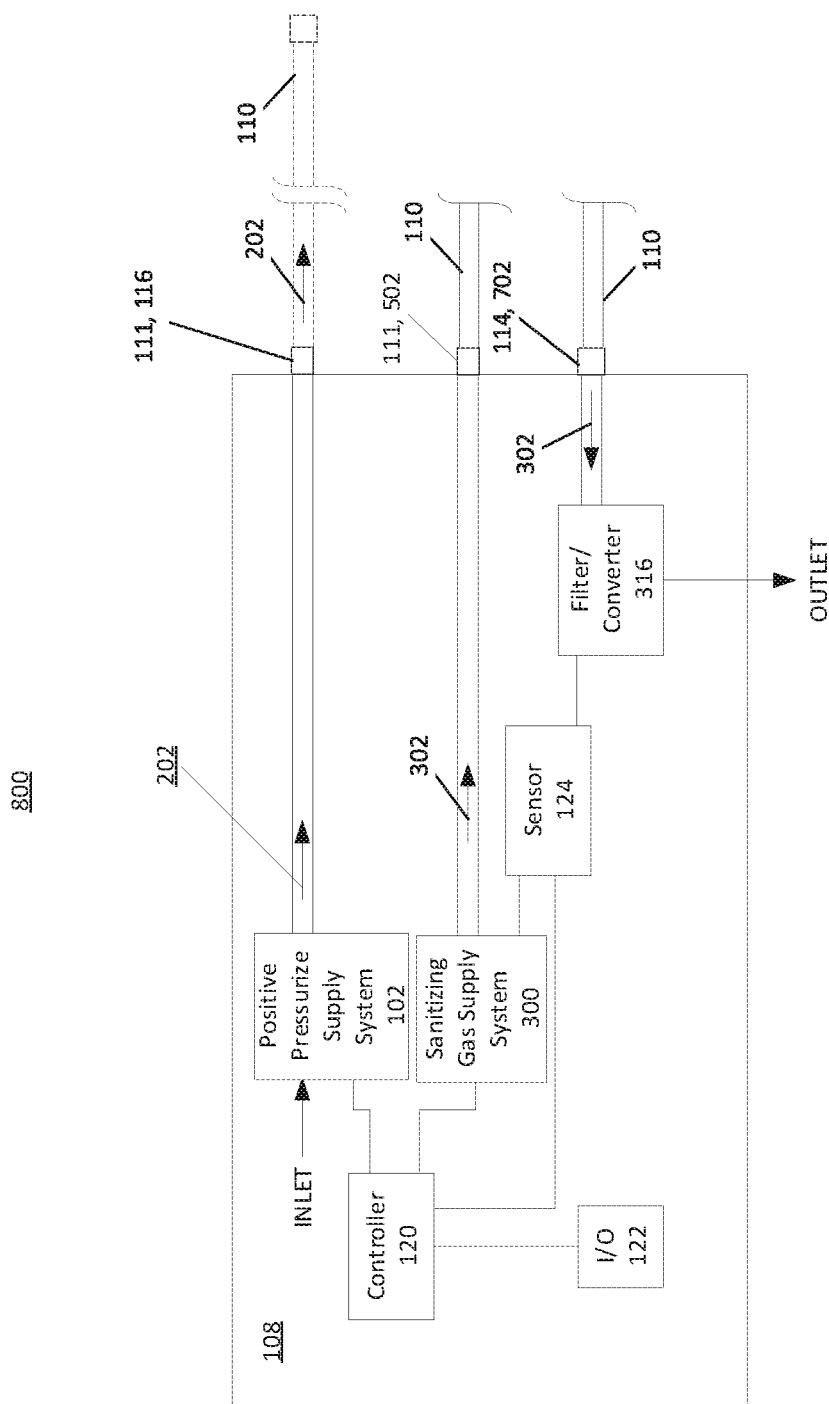
FIG. 8 is schematic view of a yet further example of a positive pressure supply system and sanitizing system of FIG. 1 consistent with the present disclosure.

With reference to FIG. 8, a further example of a self-sanitizing system 800 consistent with FIG. 1 of the present disclosure is generally illustrated. The self-sanitizing system 800 of FIG. 8 may be similar to the self-sanitizing system 700 of FIG. 7; however, the self-sanitizing system 800 may have a PAP connector 116 configured to be fluidly coupled to the first hose connector 111 for providing the pressurized air flow 302 to the hose 110 and a separate sanitizing gas outlet/connector 502 (similar to FIG. 5) configured to be fluidly coupled to the first hose connector 111 for providing the sanitizing gas 302 to the hose 110. The PAP connector 116, sanitizing gas outlet/connector 502, sanitizing gas filter/converter 316, the positive pressure supply system 102, and/or the sanitizing gas supply system 300 may be at least partially disposed within the PAP base unit housing 108.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A self-sanitizing positive airway pressure (PAP) system, comprising:
    a continuous positive airway pressure (CPAP) device configured to generate a flow of pressurized air;
    a PAP delivery system configured to be fluidly coupled to the CPAP device, the PAP delivery system comprising a hose and a mask;
    a sanitizing system configured to sanitize one or more components of the self-sanitizing PAP system, the sanitizing system comprising a sanitizing gas generator configured to generate a sanitizing gas and one or more valves downstream of the sanitizing gas generator and upstream of the CPAP device;
    one or more controllers configured to regulate CPAP operations of the CPAP device and sanitization operations of the sanitizing system to at least prevent simultaneous performance of said CPAP operations and said sanitization operations, wherein the one or more controllers are configured to regulate the one or more valves to prevent the sanitizing gas flowing to the CPAP device and/or the PAP delivery system during CPAP operations; and
    a PAP base unit housing, wherein one or more components of the CPAP device, the one or more controllers, and the sanitizing gas generator and one or more valves of the sanitizing system are disposed at least partially within the PAP base unit housing.

2. The self-sanitizing PAP system of claim 1, further comprising at least one fluid transfer device configured to generate both the flow of pressurized air and a flow of sanitizing gas.

3. The self-sanitizing PAP system of claim 2, wherein the sanitizing system configured to sanitize at least a portion of the at least one fluid transfer device.

4. The self-sanitizing PAP system of claim 1, further comprising a first fluid transfer device configured to generate the flow of pressurized air and a second fluid transfer device configured to generate a flow of sanitizing gas.

5. The self-sanitizing PAP system of claim 4, wherein the sanitizing system is configured to sanitize at least a portion of the first fluid transfer device.

6. The self-sanitizing PAP system of claim 1, wherein the CPAP device includes a humidifier, and wherein the sanitizing system is configured to sanitize at least a portion of the humidifier.

7. The self-sanitizing PAP system of claim 6, wherein the humidifier is disposed within the PAP base unit housing.

8. The self-sanitizing PAP system of claim 7, wherein the humidifier comprises a reservoir and the sanitizing system further includes a diffuser disposed in the reservoir.

9. The self-sanitizing PAP system of claim 8, wherein when liquid is in the reservoir, the diffuser is configured to distribute the sanitizing gas within the liquid.

10. The self-sanitizing PAP system of claim 1, wherein the sanitizing system is configured such that a flow of sanitizing gas flows substantially only downstream from the CPAP device.

11. The self-sanitizing PAP system of claim 1, wherein the one or more controllers are further configured to prevent performance of said CPAP operations at least in part in response to an amount of the sanitizing gas within a portion of the self-sanitizing PAP system exceeding a threshold value.

12. The self-sanitizing PAP system of claim 1, wherein:
the sanitizing system further includes at least one sanitizing gas filter or converter configured to absorb the sanitizing gas or convert the sanitizing gas into an inert substance; and
the one or more controllers are configured to prevent performance of said sanitization operations at least in part in response to a signal from a sensor associated with the sanitizing gas filter or converter.

13. The self-sanitizing PAP system of claim 1, wherein:
the PAP base unit housing includes a PAP base connector configured to be removably fluidly coupled to a first hose connector of the hose;
the PAP base connector is fluidly coupled to the CPAP device to provide the flow of pressurized air to the hose; and
the sanitizing system is configured to provide a flow of sanitizing gas through the PAP base connector.

14. The self-sanitizing PAP system of claim 1, wherein:
the PAP base unit housing includes a PAP base connector configured to be removably fluidly coupled to a first hose connector of the hose;
the PAP base connector is fluidly coupled to the CPAP device to provide the flow of pressurized air to the hose;
and wherein the PAP base unit housing further includes a sanitizing gas connector fluidly coupled to the sanitizing gas supply system to provide a flow of sanitizing gas to a sanitizing gas outlet/connector, the sanitizing gas connector configured to be removably fluidly coupled to the first hose connector of the hose.

15. The self-sanitizing PAP system of claim 1, wherein:
the hose includes a first hose connector configured to be fluidly coupled to the CPAP device and a second hose connector disposed at opposite end configured to be fluidly coupled to the PAP mask; and
the self-sanitizing PAP system further comprises a sanitizing chamber configured to be fluidly coupled to at least the second hose connector.

16. The self-sanitizing PAP system of claim 15, wherein the sanitizing chamber is at least partially within the PAP base unit housing.

17. The self-sanitizing PAP system of claim 16, wherein the sanitizing system further includes at least one sanitizing gas filter or converter configured to absorb the sanitizing gas or convert the sanitizing gas into an inert substance, the at least one sanitizing gas filter or converter being at least partially within the PAP base unit housing.

18. The self-sanitizing PAP system of claim 15, wherein the sanitizing chamber is at least partially within a sanitizing housing, the sanitizing housing being separate and distinct housing from the PAP base unit housing.

19. The self-sanitizing PAP system of claim 18, wherein the sanitizing system further includes at least one sanitizing gas filter or converter configured to absorb the sanitizing gas or convert the sanitizing gas into an inert substance, the at least one sanitizing gas filter or converter being at least partially within the sanitizing housing.

20. The self-sanitizing PAP system of claim 15, wherein the sanitizing chamber is configured to receive the PAP mask.

21. The self-sanitizing PAP system of claim 15, wherein the second hose connector is configured to be disposed within the sanitizing chamber.

22. The self-sanitizing PAP system of claim 1, wherein:
the hose includes a first hose connector configured to be fluidly coupled to the CPAP device and a second hose connector disposed at opposite end configured to be fluidly coupled to the PAP mask, and
the PAP base unit housing includes:
at least one sanitizing gas filter or converter configured to absorb the sanitizing gas or convert the sanitizing gas into an inert substance;
a PAP base connector configured to be removably fluidly coupled to the first hose connector of the hose, the PAP base connector being fluidly coupled to the CPAP device to provide the flow of pressurized air to the hose;
a sanitizing gas connector fluidly coupled to the sanitizing gas supply system to provide a flow of sanitizing gas to a sanitizing gas outlet/connector, the sanitizing gas outlet/connector configured to be removably fluidly coupled to the first hose connector of the hose; and
a sanitizing gas inlet connector fluidly coupled to the sanitizing gas filter or converter, the sanitizing gas inlet connector configured to be removably fluidly coupled to the second hose connector of the hose.

23. The self-sanitizing PAP system of claim 1, further comprising a distribution hub fluidly coupled to the sanitizing gas generator, the distribution hub configured to distribute the sanitizing gas from the sanitizing gas generator to one or more components of the CPAP device and/or PAP delivery system, wherein at least one of the one or more valves is disposed upstream of the distribution hub.

24. The self-sanitizing PAP system of claim 1, further comprising a distribution hub fluidly coupled to the sanitizing gas generator, the distribution hub configured to distribute the sanitizing gas from the sanitizing gas generator to one or more components of the CPAP device and/or PAP delivery system, wherein at least one of the one or more valves is disposed downstream of the distribution hub.

* * * * *